United States Patent [19]

Weeke

[11] 4,127,385

[45] Nov. 28, 1978

[54] ASSAY OF ANTIBODIES WITH ANTIGEN-TREATED ALUMINUM HYDROXIDE GEL

[76] Inventor: Bent Weeke, Tølløsevej 20, DK-2700 Brønshøj, Denmark

[21] Appl. No.: 690,445

[22] Filed: May 27, 1976

[30] Foreign Application Priority Data

Jun. 10, 1975 [DK] Denmark .............................. 2598/75

[51] Int. Cl.$^2$ .............................................. G01N 33/16
[52] U.S. Cl. .................................. 23/230 B; 23/230.6; 424/1; 424/12
[58] Field of Search ............. 23/230 B, 253 TP, 230.3, 23/230.6; 424/8, 12, 1, 1.5

[56] References Cited

U.S. PATENT DOCUMENTS

| 3,867,517 | 2/1975 | Ling | 424/8 |
| 3,953,588 | 4/1976 | Nieschulz | 424/12 |

OTHER PUBLICATIONS

Chemical Abstracts, 70:85739r, (1969).
Chemical Abstracts, 82:175166d, (1975).

*Primary Examiner*—Sidney Marantz
*Attorney, Agent, or Firm*—Ladas, Parry, Von Gehr, Goldsmith & Deschamps

[57] ABSTRACT

A specimen of body fluid is applied to an aluminum-hydroxide gel to which a known quantity of antigens is adhered by adsorption. Antibodies in the body fluid may be detected by determining the antigen-antibody complex adsorbed to the aluminum-hydroxide gel by means of marked anti-antibodies. A preparation of antigens adsorbed to an aluminum-hydroxide gel can be standardized by treatment with a known quantity of antibody followed by a determination of the antigen-antibody complex adsorbed to the gel by means of marked anti-antibodies.

1 Claim, No Drawings

ASSAY OF ANTIBODIES WITH ANTIGEN-TREATED ALUMINUM HYDROXIDE GEL

The present invention relates to a method of detecting antibodies in body fluids by means of known antigens or determining antigens by means of known antibodies derived from body fluids, in which a specimen of the body fluid is applied to an absorbent having a contents of antigens, whereupon the specific antibodies coupled to the antigens are determined by means of anti-antibodies.

The prior art already teaches to detect specific antibodies in body fluids by means of methods of the above said type. Hence, the specification of Danish Patent No. 120,109 suggests a method for preparing water-insoluble chemically or biologically active derivatives of peptides which by means of bridges with covalent bonds are coupled to the molecular chains in water-insoluble polymeric materials. A halocyan, such as bromocyan, is used in the method disclosed by the said patent to form the bridges. A polymeric material, such as dextran, cellulose, e.g. paper or agarose, is treated with the halocyano compound to form branched-chain groups on the molecular chains, said branched chain groups being capable of reacting with the amino groups of peptides. Various selected antigens may be coupled to the said branched-chain groups to obtain absorbents capable of selectively absorbing specific antibodies from the body fluids, i.e. the antibodies corresponding to the subject antigens.

It is possible in practice to couple to the polymer optional specific antigens so as to obtain absorbents having selective absorptive capacity with respect to the corresponding antibodies. This method is suitable for detecting whether a given body fluid contains antibodies corresponding to one or more specific antigens. Detection of the absorbed antibodies may be effected through the coupling of marked anti-antibodies, e.g. antibodies marked with radioactive isotopes which are then determined by means of isotope counting equipment. Such a method of analysis has been developed in practice and is known under the name of RAST, this being short for Radio-Allergo-Sorbent Test, and is used for diagnosing allergic reactions by determining the contents of the individual specific allergen antibodies in the body fluids, particularly blood serum. These antibodies, which are immunoglobulins, may be of the IgE, IgC, IgA, IgM and IgD types.

The known method of analysis and diagnosis outlined suffers from various drawbacks. Hence, preparation and pretreatment of the absorbent are cumbersome and time-consuming as complex synthetic methods require that branched chains be coupled to the molecular chains of the polymer. Use of halocyan for this purpose is unpleasant and risky because of the poor stability and high toxicity of these reagents. Also, there is required a substantial amount of allergen.

The present invention is based on the discovery that it is not necessary to couple the antigens to the polymeric chains via bridging branched-chain groups and that using aluminium-hydroxide gel, being an absorbent known per se, will accomplish such effective bonding to antigens that it is made possible in a simple manner to carry out quantitative determinations.

The method according to the invention is characterized by treating a specimen of the body fluid with aluminium-hydroxide gel to which the antigens are adhered by absorption and detecting or determining the specific antibodies coupled to the antigens by means of marked anti-antibodies.

Aluminium-hydroxide gel is commercially available at a low price and is non-toxic and safe to use. The coupling or adsorption of the antigens by the gel is easy to carry out and considerably quicker than in case of the known absorbents based on paper or Sephadex. The method has likewise proved economical with respect to allergen, it being possible to carry out from 50 to 100 times as many analyses based on amount of allergen than in the known RAST method. The method suggested according to the invention is flexible and uses the same allergens as are desired for other diagnosing, e.g. administered to the skin as skin tests or placed in the sick organ in the case of provocative tests. The aluminium-hydroxide gel coupled to the allergens may after sterilization and toxocological studies be used, if desired, for hyposensitizing treatment.

In the claimed method the antibodies are determined preferably by means of isotope marked anti-antibodies, this method being quick and convenient with a high degree of accuracy. However, if desired, other forms of marking may be employed, such as fluorescent marking or enzymatic coupling.

One aluminium-hydroxide gel which has proved suitable for carrying out the claimed method is a product commercially available under the trade-mark Alhydrogel (belonging to Superfos AKI A/S).

Admittedly, it is known that aluminium-hydroxide gels have a highly absorbent effect on many organic compounds such as polypeptides, e.g. also allergens, and that the gel has the effect of an adjuvant, cf. Danish Pat. No. 123,690. Furthermore, the specification of U.S. Pat. No. 3,798,319 teaches to prepare therapeutic and diagnostic antigenic or allergenic extracts that are isolated as a dry powder which is then, if desired, fixed to aluminium hydroxide to form a slowly releasing or delayed-action preparation. However, it has not been recognized heretofore that gels of this type may be used to obtain antigenous absorbents suitable for coupling to specific antibodies in body fluids, and that this will result in a reliable method of analysis for diagnosis of allergy in body fluids and quality control of allergenic extracts.

For detecting antibodies in body fluids there is used, as stated, gels that have taken up the specific antigen or antigens with respect to which it is desired to detect the patient's allergic reaction. This has made it possible in a short time to test allergic reactions to a great number of different antigens.

The method is likewise suitable for determining the nature or amount of antigens by means of fluid samples containing known antibodies. The method may therefore serve as an aid in selecting or controlling the strength and quality of the preparations to be used therepeutically against certain forms of allergy.

The method according to the invention will be illustrated below by means of some examples.

EXAMPLE 1

0.2 ml of allergen extract from dog's hair in a concentration of 1:20 (prepared by extracting 1 part of dog's hair to 20 parts of salt-water, w/v) is mixed with 0.05 ml of 2% aluminium-hydroxide gel (Alhydrogel ®, Superfos A/S) and 1.75 ml of acetate-acetic acid buffer, pH=7, 0.1 M/l (hereinafter A/E buffer for short). The mixture is mechanically turned over in a blood turning apparatus about 30 times per minute for totally 15 minutes at room temperature. The mixture is then centrifuged at 3000 r.p.m. (corresponding to about 2000 g) for two minutes. The supernatant is carefully removed by suction and replaced by 2.5 ml of A/E buffer. The liquid is again removed by suction and replaced by another batch of 2.5 ml of A/E buffer, and this procedure is repeated totally four times. After the last repeat the precipitate is redissolved in 2 ml of A/E buffer admixed with 0.3% of bovine serum albumin (Sigma) and 1% Tween 20, which is a sorbate (hereinafter A/E buffer+BSA+Tw for short). This mixture is used at once or kept at 4° C. for use at a later stage. In use there is removed 0.1 ml of mixture which is introduced to a plastic tube and admixed with 0.1 ml of serum derived from a patient. The mixture is left to stand for at least six hours at room temperature, is then centrifuged at 2000 g for two minutes, excessive supernatant is sucked away and replaced by 2.5 ml of A/E buffer+BSA+Tw. Centrifugation is repeated after mixing, the supernatant is sucked away and buffer is added; this procedure is repeated totally four times. After the last time there is added 0.05 ml of $^{125}$I-marked anti-IgE (corresponding to about 5 nannoCi of a solution containing 2.5 mCi per mg of anti-IgE). The mixture is left to stand at room temperature for at least 20 hours, whereupon the non-latent activity is removed by centrifugation at 2000 g for two minutes, the supernatant is sucked away and 2.5 ml of A/E buffer+BSA+Tw are added, after which centrifugation, removal by suction and admixture are repeated four times in all. After the last time the latent $^{125}$I activity is counted by means of a gamma counter, the aim being a count number of about 10,000 for a positive serum containing specific antibodies and 1000 as representing the normal. This is frequently the case with a totally added count number of 50,000. The contents of specific antibody against dog's hair of the unknown sera are expressed as the activity in the said analysis in relation to the activity of a normal serum (background record) and a serum having a known contents of antibody.

Tests of a number of patient's sera with respect to various allergen extracts proved agreement of the results of the said method with the known RAST method with identical allergens coupled to paper discs.

EXAMPLE 2

2 allergen extracts from grass pollen phleum pratense (cat's tail) having a concentration of 1:20 (weight of pollen starting material to volume of 0.9% salt-water) are adhered by absorption to aluminium-hydroxide gel and are compared by means of a serum derived from a patient allergic to grass pollen having a known contents of antibody against grass pollen. 0.2 ml of extracts A and B respectively (short for the two grass pollen extracts) is added in the manner specified in Example 1 to 0.05 ml of 2% Alhydrogel and 1.75 ml of A/E buffer. The mixture is rotated for 15 minutes in a blood turning apparatus at about 30 r.p.m. at room temperature. After centrifugation at 3000 r.p.m. (about 2000 g) for two minutes the supernatant is carefully sucked away and replaced by 2.5 ml of A/E buffer which is again sucked away, etc., repeated four times in all. After the last time the precipitate is redissolved in 2 ml of A/E buffer+λ BSA+Tw. There are prepared a number of dilutions from these solutions, these being prepared as diluted 1, 10, 100, 1000 and 10,000 times by means of A/E buffer+BSA+Tw. There are transferred from the undiluted solution and the diluted solutions 0.1 ml samples to plastic tubes and these are admixed with 0.1 ml of serum having a known contents of antibody against phleum pratense. As in Example 1 the mixture is left to react for at least six hours at room temperature (18°–24° C.), it is centrifuged, etc., four times in all. After the last time there is added 0.05 ml of $^{125}$I-anti-IgE (Phadebas RAST, Pharmacia, Uppsala or similar radioactively marked antibody), and the mixture is left to react for at least 20 hours at room temperature. The mixtures are then centrifuged at 2000 g for two minutes, non-latent activity is removed by suction, followed by washing and centrifugation as specified in Example 1, totally four times, and the remaining latent $^{125}$I activity is counted by means of a gamma counter. Based on the count numbers of the various dilutions of the extracts A and B these may be compared. Also in this case there is included in the analysis a serum derived from a normal person without any contents of specific antibody against phleum pratense (as background value).

EXAMPLE 3

Based on an allergen extract from horsehair and scale in a concentration of 1:20 (weight of horsehair/scale to volume of 0.9% salt-water) are prepared a number of diluted solutions which are adhered by absorption to aluminium-hydroxide gel, and by means of a serum derived from a patient allergic to horsehair is determined a characteristic S-shaped curve, from which it is possible to assess the strength of bonded allergen from the extract.

Based on an extract of horsehair/scale 1:10 a number of tenfold dilutions are made with 0.9% sodium chloride. 0.05 ml of the solutions prepared is each mixed with 0.05 ml of 2% Alhydrogel and 1.9 ml of 0.9% sodium-chloride solution. The mixtures are rotated for 15 minutes in a blood turning apparatus at 30 r.p.m. at room temperature. After centrifugation at 3000 r.p.m. (about 2000 g) for two minutes the supernatant is carefully sucked away and replaced by 2.5 ml of 0.9% sodium-chloride solution which is again sucked away, etc., repeated totally four times. After the last time the precipitates are redissolved in 5 ml of 0.9% sodium-chloride solution. 0.05 ml of each of these solutions is mixed with 0.05 ml of serum derived from a patient allergic to horsehair, and as a check, serum derived from a non-allergic patient (background).

The mixtures are reacted for at least six hours at room temperature (18°–24° C.), followed by centrifugation, etc., four times in all, as in Example 1. After the last time is added 0.05 ml of $^{125}$I-anti-IgE (Phadebas RAST, Pharmacia Uppsala or similar radioactively marked antibody), and the mixtures are left to react for at least 20 hours at room temperature.

The mixtures are then centrifuged at 2000 g for two minutes, non-latent radioactivity is removed by suction, followed by washing and centrifugation as specified in Example 1, four times in all, and the remaining $^{125}$I activity is counted by means of a gamma counter.

Based on the count numbers of the various dilutions of the extracts and their dilutions there is drawn a characteristic curve for extract from horsehair and scale. Also in this case there is included in the analysis a serum derived from a normal person having no contents of specific antibody against horsehair/scale (as background value).

The analysis described in this example is suitable for characterizing a specific extract, including determining to which extend the allergen extract could be diluted before use and still provide maximum bonding of specific antibody and with that count number. The analysis is likewise suitable for comparing the strength of allergen extracts of the same type, but obtained in different manners.

Also, this method may be used to determine the storage life of the allergen extracts.

EXAMPLE 4

A reference system including an extract from horsehair and scale and dilutions of a serum derived from a patient allergic to horsehair will in a double logarithmic coordinate system appear as a linear function which is suitable as reference curve in carrying out the method.

0.05 ml of extract from horsehair and scale is introduced to a plastic tube and mixed with 0.05 ml of 2% aluminium hydroxide and 2 ml of TRIS 0.1 M, pH=7.5 with 1% Tween 20 (hereinafter TRIS-T for short).

The mixture is left to stand at room temperature for 15 minutes. Not bonded constituents are then removed by centrifugation at 2000 g for two minutes, followed by careful suction of most of the free supernatant, the latter part thereof being most conveniently removed by carefully turning the plastic tube upside down and dispensing the free liquid. This procedure is repeated three times subject to addition of 2.5 ml of TRIS-T, centrifugation, suction and dispensation as described.

The "washed" precipitate remaining after the last dispensation is redissolved in 5 ml of TRIS-T, and 0.05 ml is distributed among small plastic tubes, followed by adding 0.05 ml of serum dilutions.

The serum dilutions are obtained by mixing the positive serum derived from the patient allergic to horsehair (fixed at 100% in the reference system) with normal serum from one or more non-allergic persons (fixed at 0% in the reference system) in the ratios (v/v):1+0, 1+4, 1+24 and 1+49 (equal to the concentrations of specific antibody: 100%, 20%, 4% and 2%).

The serum reaction is effected for three hours at room temperature (or preferably overnight, i.e. for 18 to 22 hours). This is followed by removal of not bonded serum constituents by adding 2.5 ml of TRIS-T, centrifugation at 2000 g for two minutes and careful suction of the supernatant, although there should be left from 0.2 to 0.3 ml of free supernatant to prevent stirring up precipitate during the suction step. There is again added 2.5 ml of TRIS-T, followed by centrifugation and suction, repeated totally three times. After the last careful suction the remainder of free supernatant is removed by carefully turning all the tubes upside down.

The "washed" precipitate is admixed with 0.05 ml of $^{125}$I-anti-IgE (Pharmacia Phadebas RAST isotope unit or similarly marked antibody), and the mixture is left to react for at least 20 hours at room temperature. After adding 2.5 ml of TRIS-T to all the tubes the mixtures are centrifuged at 2000 g for two minutes and non-latent activity is removed by suction, washing and centrifugation as described above. This washing procedure is repeated four times in all, and the remaining latent $^{125}$I activity is counted be means of a gamma counter.

Based on the count numbers ($y$ values) and the serum dilutions ($x$ values) the linear relation is reproduced in a double logarithmic coordinate system according to the principle of least distance. Based on the count numbers unknown sera may be determined as specific antibody and other allergen/serum systems may likewise be stated in relation to this horsehair and scale/patient reference system.

What I claim is:

1. A method of detecting or determining antibodies in body fluids comprising:
   (a) providing an aluminum hydroxide gel previously contacted with antigen for which said antibodies are specific;
   (b) contacting a sample of the body fluid with the antigen-treated aluminum hydroxide gel of a) so that, if said specific antibodies are present in the body fluid, antigen-antibody complex will form on said antigen-treated gel;
   (c) contacting the aluminum hydroxide gel resulting from b) with labeled anti-antibodies specific to said antibodies;
   (d) measuring the amount of labeled anti-antibodies bound to any antigen-antibody complex formed on the aluminum hydroxide gel as a result of (c); and
   (e) correlating the measurement of (d) to the presence of any said specific antibodies in the body fluid.

* * * * *